(12) United States Patent
Aoyagi et al.

(10) Patent No.: US 8,546,075 B2
(45) Date of Patent: *Oct. 1, 2013

(54) METHOD OF DETECTING HEPATITIS C VIRUS

(75) Inventors: Katsumi Aoyagi, Wako (JP); Kumiko Iida, Wako (JP); Naoko Matsubara, Wako (JP)

(73) Assignee: Advanced Life Science Institute, Inc., Saitama (JP)

(*) Notice: Subject to any disclaimer, the term of this patent is extended or adjusted under 35 U.S.C. 154(b) by 517 days.

This patent is subject to a terminal disclaimer.

(21) Appl. No.: 10/577,853

(22) PCT Filed: Oct. 28, 2004

(86) PCT No.: PCT/JP2004/016377
§ 371 (c)(1),
(2), (4) Date: Oct. 17, 2007

(87) PCT Pub. No.: WO2005/040815
PCT Pub. Date: May 6, 2005

(65) Prior Publication Data
US 2008/0044807 A1   Feb. 21, 2008

(30) Foreign Application Priority Data
Oct. 28, 2003  (JP) .................................. 2003-367783

(51) Int. Cl.
*C12Q 1/70* (2006.01)
(52) U.S. Cl.
USPC .................................. 435/5; 435/962; 436/18
(58) Field of Classification Search
None
See application file for complete search history.

(56) References Cited

U.S. PATENT DOCUMENTS

| | | | |
|---|---|---|---|
| 4,609,630 A | 9/1986 | Yanovsky | |
| 4,703,001 A | 10/1987 | Vodian et al. | |
| 5,306,622 A | 4/1994 | Mangold | |
| 5,773,212 A | 6/1998 | Figard | |
| 6,727,092 B2* | 4/2004 | Stewart et al. | 435/320.1 |
| 7,026,110 B1 | 4/2006 | Veriac et al. | |
| 2002/0037868 A1* | 3/2002 | Budkowska et al. | 514/44 |

FOREIGN PATENT DOCUMENTS

| | | |
|---|---|---|
| EP | 0 296 336 B1 | 12/1988 |
| EP | 0 967 484 A1 | 12/1999 |
| EP | 1 020 727 A1 | 7/2000 |
| EP | 1 021 723 B1 | 7/2000 |
| EP | 1 039 297 A1 | 9/2000 |
| EP | 1 306 671 A1 | 5/2003 |
| GB | 2 016 687 A | 9/1979 |
| JP | 8-29427 A | 2/1996 |
| JP | 08-62219 A | 3/1996 |
| JP | 11-51940 A | 2/1999 |
| JP | 11-108932 A | 4/1999 |
| JP | 2001-4621 A | 1/2001 |
| JP | 3171827 B2 | 3/2001 |
| JP | 3176570 B2 | 4/2001 |
| JP | 2002-512370 A | 4/2002 |
| KR | 2000-0068705 | 11/2000 |
| WO | WO 92/11523 A2 | 7/1992 |
| WO | WO 94/13700 | * 6/1994 |
| WO | WO 99/06836 | * 2/1999 |
| WO | WO 99/06836 | * 11/1999 |
| WO | WO 00/07023 | * 10/2000 |

OTHER PUBLICATIONS

Liu et al., "Regulated Processing of Hepatitis C Virus Core Protein is Linked to Subcellular Localization," Journal of Virology, Jan. 1997, 71(1):657-662.

Office Action dated Jun. 16, 2009, in corresponding European application 04 793 357.7, 9 pages.

Huebner et al., Database Biosis Biosciences Information Services, abstract of "Fractionation and quantitative differences of glutenin from wheat varieties varying in baking quality," Cereal Chemistry, 1976, 258-269, 1 page.

Schwartz et al., "Loss of hereditary uterine protoprophyria through chromosomal rearrangement in mutant Rhode Island red hens," Int. J. Biochem., 1980, 12:935-940.

Aoyagi et al., "Development of a Simple and Highly Sensitive Enzyme Immunoassay for Hepatitis C Virus Core Antigen," J. Clin. Microbiol., Jun. 1999, 37(6):1802-1808.

Nishanian et al., "A Simple Method for Improved Assay Demonstrates that HIV p24 Antigen is Present as Immune Complexes in Most Sera from HIV-Infected Individuals," Journal of Infectious Diseases, 1990, 162:21-28.

Pace et al., "Optimization of Immunohistochemical Reactions," Immunohistochemical Staining Methods, 2009, Chapter 16, 109-114.

Sigma, "Trizma®HCl Specification Comparison," found Jul. 1, 2011, 1 page.

* cited by examiner

*Primary Examiner* — Michelle S Horning
(74) *Attorney, Agent, or Firm* — Foley & Lardner LLP

(57) ABSTRACT

A method of treating samples containing hepatitis C virus (HCV) which method comprises treating HCV-containing samples with a treating agent containing (1) an acidifying agent, and (2) a protein-denaturing agent, or an amphoteric surfactant or a cationic surfactant having both a straight chain alkyl group of 10 or more carbon atoms and a tertiary amine or a quaternary ammonium salt in the same molecule, to effect the release of the HCV antigen and the inactivation of antibodies that bind to the HCV antigen, and the like.

11 Claims, 2 Drawing Sheets

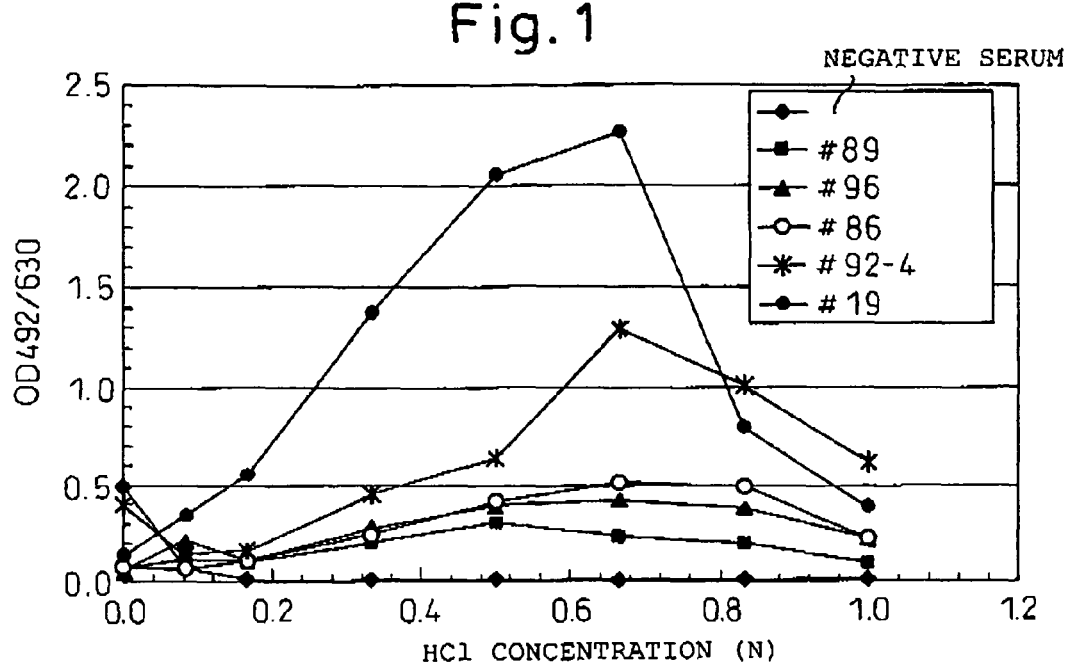
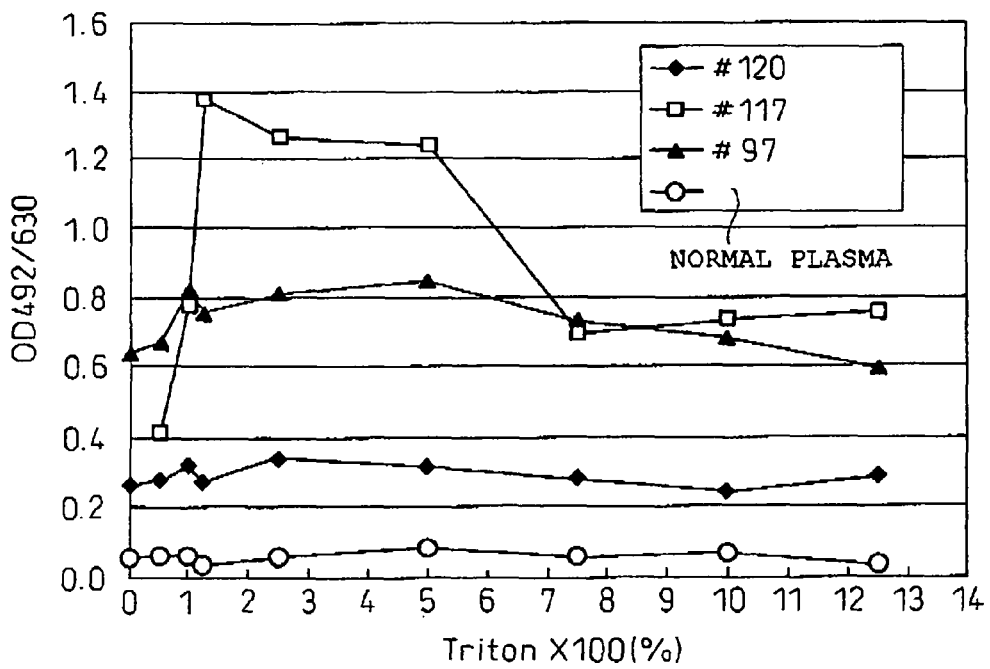

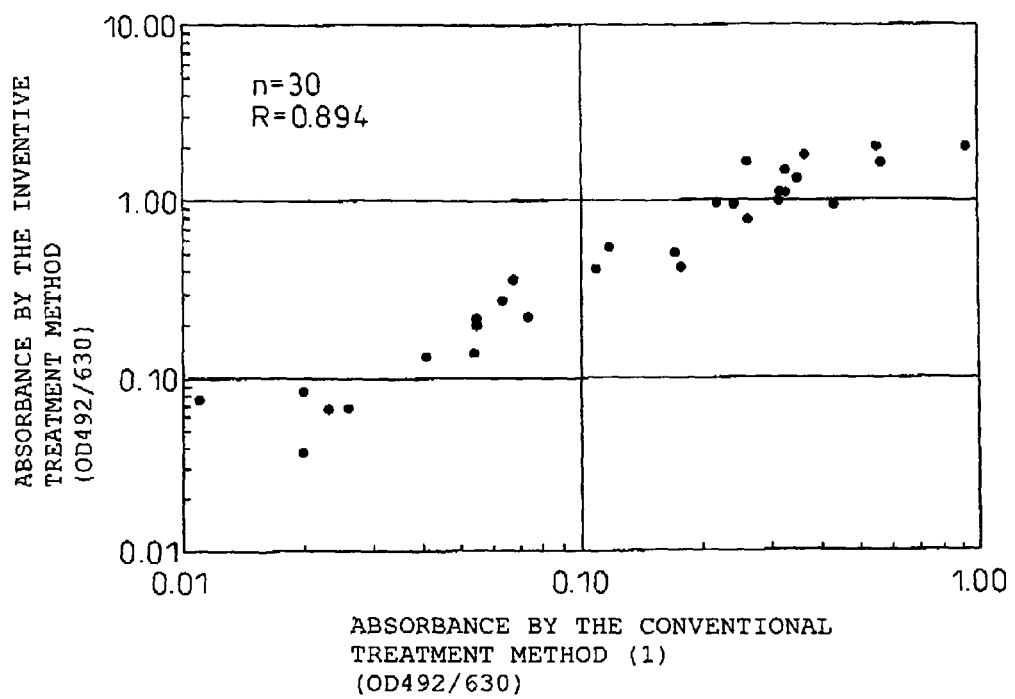

METHOD OF DETECTING HEPATITIS C VIRUS

TECHNICAL FIELD

The present invention relates to a method for detecting or quantifying hepatitis C virus (HCV)-related antigen in the serum as well as a very simple and reliable method of treating samples for use in such detection and quantification of HCV antigen.

BACKGROUND ART

As the amount of HCV in the body is limited and an in vitro proliferation system of HCV has not been established, an anti-serum for HCV by using native virus particles or purified virus proteins has not been obtained. The individuals produce different antibodies to the antigen in their serum and the epitopes of the antibodies are different individually. Furthermore, as in human serum, antibodies against substances other than HCV may be contained. We must judge the result of HCV antibody testing considering sufficiently the cross reactivity etc.

As antibodies may have not been produced immediately after HCV infection, the antibody to HCV proteins cannot be detected by antibody testing during the period called "the window period" before the emergence of antibodies in the blood. For the treatment of patients with hepatitis C, various interferons and ribavirin may be effective, but the antibody test alone is not sufficient for the selection of therapeutic regimens and for monitoring disease conditions of patients. Under these circumstances, attention has been focused on methods of detecting HCV antigens and genes including definitive diagnosis.

As methods of detecting the HCV gene, the nucleic acid amplification technique (NAT) and the DNA probe method are known and are widely used in clinical settings. Though the NAT technique is highly sensitive, it also has several difficult problems. For example, in order to carry out a polymerase chain reaction (PCR) method, reverse transcription into DNA is required because HCV is a RNA virus, and a loss may easily occur during transcription from RNA to DNA; contamination may easily occur; a large quantity of specimens cannot be processed at one time since special equipment for amplification etc. is required and the procedure is complicated; and the cost for testing is expensive, and the like. In other NAT's as well, special equipment for amplification etc. is required and the cost for testing is enormous. The DNA probe method is not sensitive enough and requires about 20 hours before results can be obtained (IGAKU TO YAKUGAKU (Japanese Journal of Medicine and Pharmacological Sciences) 31:961-970, 1994).

A major problem in methods for detecting the HCV gene is the poor stability of HCV RNA in test samples, and it has been pointed out that the determined values may decrease by the step of obtaining the serum, storage for medium to long periods, and freeze-thaw procedures. This reason, it is believed, is that any damage to the surface of HCV particles may trigger the ribonuclease (RNase) in the blood resulting in easy degradation of HCV RNA as well. Therefore, in order to perform the HCV RNA test routinely, we must take care the handling and storage.

As a method of detecting HCV, attention has been focused on the method of detecting the HCV antigen in addition to HCV RNA.

As methods of detecting the HCV antigen, as described in Japanese Unexamined Patent Publication (Kokai) No. 8-29427, attempts have been made to detect the core antigen in the serum using a monoclonal antibody that has a specificity for an epitope on the HCV core antigen. Though this method is inexpensive and offers results in a short period of time (about 3 hours) as compared to the PCR method, it has several serious problems in the practical use.

Thus, for the treatment of test samples (serum), it requires multi-stage processing such as the polyethylene glycol treatment (4° C. for 1 hour), centrifugation (15 minutes), supernatant removal, urea treatment, alkali treatment (30 minutes), and the addition of a neutralizing agent. As the procedure is complicated as described above, experience is required in order to obtain reproducible results and, besides, as treatment for two hours is required, a large quantity of samples cannot be processed at one time.

Because of the required steps of centrifugation, supernatant removal etc., it is very difficult to automate the procedure. In addition, it is 10 to 100-fold less sensitive than the PCR method, and, therefore, is low in clinical usefulness. According to Journal of Hepatology 23:42-45, 1995, the detection limit of this assay is in between $10^4$-$10^5$ copies of HCV RNA/ml, and IGAKU TO YAKUGAKU (Japanese Journal of Medicine and Pharmacological Sciences) 6:1065-1070, 1996, describes that when the sera of 102 patients with chronic hepatitis C before treatment were measured, it only gave a positivity of 67% which is almost equal to the of the above-mentioned DNA probe method, in contrast to a 100% positivity by the competitive reverse transcription (CRT)-PCR method. Thus there was much room for improvement in terms of sensitivity.

The two methods for detecting the HCV antigen described in Japanese Patent No. 3176570 and Japanese Patent No. 3171827 do not require multi-stage processing, including centrifugation etc., which is a drawback of the above HCV antigen detection method in Japanese Unexamined Patent Publication (Kokai) No. 8-29427; are able to process HCV-containing specimens in only one or two steps for 30 minutes; and are able to detect HCV antigen at a high sensitivity. In addition, as the procedure has been simplified, it is possible to process a large quantity of samples at one time and reproducibility and accuracy are enhanced as well. Furthermore, this measurement method can give results at a lower cost and in a shorter period of time as compared to NAT.

However, it is necessary to develop a more clinically useful method which satisfies all aspects of high sensitivity, specificity, reproducibility, easy handling, a shorter processing time, and low cost.

Though the two methods of detecting the HCV antigen described in Japanese Patent No. 3176570 and Japanese Patent No. 3171827 require 30 minutes of sample processing time, a shorter processing time is further desired.

In particular, the point of care testing (POCT) is rapidly growing in the US where the streamlining of hospital management is in progress, and is expected to be introduced in Japan and other countries in the future. This is a method in which testing is performed at a site near the patient, the test result is immediately judged by the attending doctor, necessary treatment is administered immediately, and even the progress of treatment and monitoring of prognosis are made, and thus it is attracting attention as it could serve the purpose of greatly enhancing the quality of medical care. Compared to testing performed in the central clinical testing laboratory, POCT can reduce the cost related to sample transportation and testing equipment, and patients can receive testing and immediate treatment at one visit, thereby reducing the patient's burden. In order to respond to these needs in the future, sample processing time must be curtailed as much as possible.

Furthermore, as there are very few HCV particles and thus very little HCV antigen in the blood of patients with HCV infection, a more sensitive method of detection is desired.

Patent document 1: Japanese Unexamined Patent Publication (Kokai) No. 8-29427
Patent document 2: Japanese Patent No. 3176570
Patent document 3: Japanese Patent No. 3171827
Patent document 4: Japanese Unexamined Patent Publication (Kokai) No. 8-29427
Patent document 5: Japanese Patent No. 3176570
Non-patent document 1: IGAKU TO YAKUGAKU (Japanese Journal of Medicine and Pharmacological Sciences) 31:961-970, 1994
Non-patent document 2: Journal of Hepatology 23:42-45, 1995
Non-patent document 3: IGAKU TO YAKUGAKU (Japanese Journal of Medicine and Pharmacological Sciences) 6:1065-1070, 1996

DISCLOSURE OF THE INVENTION

There are very few HCV particles and thus very little HCV antigen in the blood of patients with HCV infection. It is also estimated that many of the infected individuals (carriers) progress to cirrhosis and/or hepatic cancer in 10-30 years, and thus early diagnosis and early treatment are important. The understanding of pathological conditions for the treatment and the estimation of prognosis of patients with HCV infection is also important, and the assay of more significant HCV-related markers (antigen) is highly desired. Also more clinically useful methods of determination face the challenges of sensitivity, specificity, reproducibility, reduction in time of measurement, ease of handling (full automation), and lower cost, and it is necessary to develop a more clinically useful method which satisfies all of them.

Thus, there are needs for the development of methods of obtaining HCV particles in particular HCV antigen in the serum in a simple manner and at a high yield, and of highly sensitive methods of detecting and quantifying them.

Thus, it is an object of the present invention to provide a highly sensitive method of detecting and quantifying HCV antigen that is suitable for processing in a short period of time (simply) a large quantity of samples for screening purposes such as physical checkup using temperature that is usable in a common fully automated determination instrument.

Thus, it is an object of the present invention to provide a HCV antigen-detecting and quantifying method that can be adapted for a common fully automated determination instrument by providing a processing method that releases the HCV antigen in a sample in a short period of time, in a simple manner, and without using high temperature with a sensitivity equal to or better than NAT. It is also an object of the present invention to provide a highly sensitive detection and determination method using a monoclonal antibody that specifically recognizes HCV antigen and a hybridoma that produces said monoclonal antibody.

MEANS TO SOLVE THE PROBLEMS

As the blood levels of HCV in infected individuals are very low ($10^2$-$10^7$ copies/ml), a very high sensitivity is required to detect the virus antigen. Generally, in immunoassays represented by the use of antibody as a probe for capturing the target antigen, possible methods of enhancing detection sensitivity include: 1) to increase the number of the target antigen molecules, 2) to increase the binding ability of the probe that binds to the target antigen and to increase the amount of the probe, 3) to reduce non-specific reactions, and 4) to increase the signal intensity to be used in detection, and by combining these methods, a higher sensitivity can be attained.

Though the structure of HCV has not been clarified yet, it is estimated, based on the structure of related flaviviruses and general information on common viruses, that HCV particles in the blood are present with the genomic RNA being packed with the core antigen and are encircled by coat proteins comprising the envelope antigen (E1, E2) anchoring on the lipid membrane so as to encircle it. It is reported that HCV particles in the blood occur in association with low density lipoprotein (LDL), and besides, as host-derived antibodies are present against the envelope antigen in the blood, it is estimated that HCV particles and the antibody against the envelope antigen bind to each other and occur as an immune complex.

Also, there are mostly host-derived antibodies against HCV antigen in the blood, and thus they are expected to compete with the capture probe and/or the detection probe when detecting the HCV antigen. Unless otherwise specified in the present application, HCV antigen means a protein encoded by the HCV genomic RNA. Thus, it includes probable structural proteins such as the core antigen, the E1 antigen and the E2 antigen, or probable non-structural proteins such as NS2, NS3, NS4 and NS5 antigens, and the like.

In test samples containing the HCV antigen, there can be seen virus particles and immune complexes formed by the HCV antigen and the antibody. For example, in order to detect the HCV core antigen, it is necessary to: I) destroy HCV particles so as to release the core antigen from the HCV particle as well as to convert the core antigen into monomers as much as possible, II) inactivate or remove the host-derived antibodies against the HCV antigen, and III) dissociate the core antigen from the interaction with blood components other than the antibody against the HCV antigen. In order to remove the antibody against the HCV antigen, the centrifugation step or the affinity column step is needed, but it requires more processing steps, and thus inactivation is desired.

Thus, release as much as possible into monomer form of the core antigen contained in the limited amount of samples in a given detection system from the HCV particle, antibodies against the HCV antigen, other blood components etc. increases the number of antigen molecules that can react with the probe. The present invention realizes higher reactivity with the probe by a brief and simple treatment of samples to liberate into the monomer form as much as possible.

Therefore, one of the inventions provided by the present application lies in a treatment method which comprises allowing the HCV core antigen in a test sample to be converted into a state suitable for detection using a probe by a brief and simple procedure. Furthermore, it lies in a method which comprises inactivating, simultaneously, host-derived antibodies against the HCV core antigen that compete with the capturing probe and the detecting probe.

In accordance with the present invention, by using the indicated treatment method, the HCV core antigen present in a test sample is released from the virus particles or immune complexes and, simultaneously, human antibodies present in the test sample against the HCV core antigen are inactivated, thus enabling an easy and highly sensitive detection by an immunoassay using a probe such as an antibody.

Furthermore, in order to convert the test sample containing the HCV-related antigens into a state suitable for forming an immune complex of the HCV core antigen and a probe such as an antibody, the present invention provides a method of detecting and quantifying the HCV-related antigens which method comprises a step of treating test samples with a treating agent that effects the release of the HCV core antigen from virus particles and the inactivation of human antibodies against the HCV-related antigens simultaneously present in the test samples, and of detecting and quantifying the released HCV-related antigens by an immunoassay using a probe such as an antibody, as well as a testing kit.

The probes used for detection such as antibody may be those that specifically bind to the HCV core antigen and exhibit a certain high affinity but is, preferably, one of the probes that capture the HCV core antigen in the treated test sample recognizes and binds to the C terminal region of the HCV core antigen. As used herein the C terminal region of the HCV core antigen refers to a sequence from the amino acid at position 81 to the amino acid at position 160 of the HCV core antigen or a portion thereof. In particular, antibodies that recognize amino acids at positions 100-120, 111-130, i.e. 100-130, of the HCV core antigen are useful.

As the probe, as used herein, any molecule that exhibits a high specificity and/or affinity for the HCV core antigen can be used, for example a polyclonal antibody obtained by immunizing an experimental animal such as a mouse, a rat, a guinea pig, a rabbit, a chicken, a goat, sheep, and a cattle; a monoclonal antibody produced by a hybridoma obtained by isolating splenocytes from the immunized individual, and fusing the cells to myeloma cells to yield the hybridoma; a monoclonal antibody produced by cells obtained by immortalizing splenocytes, leukocytes in the blood with EB virus; a monoclonal antibody being produced by HCV-infected humans, chimpanzees etc.; recombinant antibody produced by cells transformed with a recombinant antibody gene that was constructed by combining a variable region gene fragment obtained from immunoglobulin cDNA or chromosomal DNA of mice, humans etc., a variable region gene fragment constructed by combining an immunoglobulin cDNA, a portion of chromosomal DNA with an artificially prepared sequence, a variable region gene fragment constructed using an artificial gene sequence, or a variable region gene fragment constructed from these materials by the gene recombinant technology with an immunoglobulin constant region gene fragment; a phage antibody constructed by the fusion of the above variable region gene fragment with, for example, a bacteriophage structural protein; a recombinant antibody produced by cells transformed with a recombinant antibody gene constructed by combining the above variable region gene fragment with a portion of another suitable gene fragment such as the myc gene; a molecule that specifically binds to a protein such as receptor or a probe obtained by modifying it; a probe prepared by the combinatorial chemistry technology, and the like.

In accordance with the present invention, a monoclonal antibody that binds to the HCV core antigen was obtained as one of the above probes. A monoclonal antibody can be prepared in the following manner. For example, BALB/c mice etc. are regularly immunized by the intraperitoneal or intradermal administration of a fusion polypeptide containing the HCV core region or a polypeptide alone or as an antigen bound to BSA, KLH etc. in conjunction with various adjuvants. When the antibody titer in the blood has increased, the antigen is administered as a boost immunization into the tail vein, and after the spleen was aseptically removed, it is subjected to cell fusion with a suitable mouse myeloma cell line to yield a hybridoma. The procedure may be carried out according to Kohler and Milstein (Nature 256:495-497, 1975).

The hybridoma cell line obtained in the above method is cultured in a suitable culture medium, and then hybridomas producing an antibody that exhibits specific reactivity with the antigen are selected and cloned. For cloning of antibody-producing hybridomas, the limiting dilution method as well as the soft agar method can be used (Eur. J. Immunol. 6:511-519, 1976). The monoclonal antibody thus produced may be purified by a method such as column chromatography using Protein A, etc. In addition to the above monoclonal antibody, molecules that are used as the probe may be prepared. For example, recombinant antibody is reviewed in detail in Hoogen boon (Trends in Biotechnology 15:62-70, 1997).

The monoclonal antibody prepared according to the present invention may be used as a testing reagent for the detection and quantification of the HCV core antigen in an enzyme-linked immunosorbent assay (ELISA), an enzyme immunodot assay, a radioimmunoassay, an agglutination-based assay, or other well known immunoassays. When a labelled antibody is used for detection, a fluorogenic substance, a chemiluminescent substance, a radioactive substance, an enzyme, a chromogenic substance etc. may be used as a labelling compound.

When, for example, a method based on a principle of the sandwich immunoassay system is used to detect an HCV-derived protein in test samples (serum), the diagnostic kit to be used may include one or more monoclonal antibodies of the present invention coated on a solid support (for example, an inner wall of a microtiter well), one or more monoclonal antibodies bound to a labelling substance, or a fragment thereof. The combination of a monoclonal antibody bound to the solid support and a labelled monoclonal antibody is arbitrary, and any combinations that provide high sensitivity may be selected.

As the solid support to be used, there can be mentioned a polystyrene, polycarbonate, polypropylene or polyvinyl microtiter plate, a test tube, a capillary, beads (latex particles, red blood cells, metal compounds, etc.), a membrane (liposome etc.), a filter and the like.

In accordance with the present invention, the core antigen in a test sample, that was treated with an acidifying agent, is determined by an immunoassay. At this time, a monoclonal antibody against the HCV core antigen was used in the determination. As shown in Examples, a detection system that used two kinds of monoclonal antibodies as the immobilized antibody and two kinds of monoclonal antibodies as the labelled antibody for detection and a detection system that used three kinds of monoclonal antibodies as the immobilized antibody and two kinds of monoclonal antibodies as the labelled antibody for detection were compared. As a result, the detection system that used three kinds of monoclonal antibodies as the immobilized antibody and two kinds of monoclonal antibodies as the labelled antibody for detection gave enhanced reactivity. This is probably because of the effect of using three kinds of monoclonal antibodies as the immobilized antibody. Thus, the present invention also provides an immunological assay method for the HCV core antigen that uses a monoclonal antibody. It indicates that reactivity is more enhanced when three kinds of antibodies are used as the immobilized antibody than when two kinds that recognize amino acids 100-120 or 111-130 of the C terminal region of the HCV core antigen are used.

BRIEF EXPLANATION OF THE DRAWINGS

FIG. 1 shows the effect of concentration of the acidifying agent (hydrochloric acid) used in sample treatment, A test sample from normal healthy subject (normal) and five HCV antigen-positive samples were used.

FIG. 2 shows the effect of concentration added of the non-ionic surfactant (Triton X-100) used in sample treatment. A test sample from normal healthy subject (normal plasma) and three HCV antigen-positive samples were used.

FIG. 3 shows the correlation of the measured values of core antigen activity liberated after HCV antigen-positive samples were treated according to the present invention and the measured values of core antigen activity liberated after they were treated according to the conventional method.

BEST MODE FOR CARRYING OUT THE INVENTION

Test samples for use in the present invention include biological fluids such as whole blood, plasma, serum, urine, saliva, and cerebrospinal fluid, and hepatic tissue.

As conditions for inactivating the activity of antibodies present in test samples, alkaline treatment, acid treatment, and the like are known. The acid treatment of serum etc. may irreversibly denature some serum proteins and may even cause precipitation or cloudiness. This may often cause clogging etc. in pipetting of test samples after the treatment, and precipitates entangling denatured proteins may adsorb to the carrier or solid phase onto which a probe such as the antibody that captures the target antigen has been bound in measurement, resulting in false-positive results. In addition, the target antigen may be entangled into those precipitates and thereby the amount of antigen capable of binding to the probe may be decreased, which causes a problem of reduced sensitivity.

By adding another substance to the acidifying agent, the present invention could attain the prevention of irreversible denaturation such as precipitation and cloudiness by acid treatment, prevention of false-positives, and enhancement in sensitivity.

As the acidifying agent as used herein, hydrochloric acid, sulfuric acid, acetic acid, trifluoroacetic acid, trichloroacetic acid etc. are suitable. Specifically, the concentration of the acidifying agent is preferably 0.13N or greater and 1N or less at the treatment and more preferably 0.5N-1N. At this time, the pH of test samples to which the acidifying agent has been added are 2.5 or less, and most test samples are treated at pH 2.0 or less.

As a substance to be added to the acidifying agent, a surfactant may be contemplated. A variety of surfactants are known to have an ability of destroying the higher structures of protein, and they have an ability of destroying the membrane of virus particles, denaturing antibody against the target antigen in test samples, and solubilizing insoluble proteins. In the presence of such a surfactant, however, the conformational epitope of the target antigen is also destroyed, and the binding with a probe such as a antigen-capturing antibody is weakened, posing a serious problem of reduced sensitivity.

On the other hand, the denaturing activity of a surfactant may often be reversible, and thus the reduction of the surfactant concentration by dilution or dialysis may recover the temporary denatured structure. This clearly means that there are test sample-derived antibodies that may compete with a target antigen-capturing probe or a detecting probe, with a result that sensitivity may be reduced. Thus, the addition of a surfactant has such an ambivalent nature. Surfactants are classified in various ways according to their structures or properties. In terms of the ionic type, there are anionic, cationic, amphoteric, nonionic, etc. surfactants.

Among these surfactants, the present inventors have found that by combining an acidifying agent, and an amphoteric surfactant or a cationic surfactant having both a straight chain alkyl group of 10 or more carbon atoms and a tertiary amine or a quaternary ammonium salt in a molecule, the problem of precipitates etc. in acid treatment and of reversible denaturing of antibodies in test samples in the surfactant treatment can be resolved, leading to remarkably enhanced sensitivity in the detection of the HCV antigen, and thereby have completed the present invention.

Furthermore, it is more preferable, the present inventors have found, to add a nonionic surfactant such as polyoxyethylene isooctylphenyl ethers such as Triton X-100 and polyoxyethylene nonylphenyl ethers such as NP40, to add a protein denaturing agent such as urea and thiourea, or to add a reducing agent such as cysteine, cysteamine, dimethylaminoethanethiol, diethylaminoethanethiol, and diisopropylaminoethanethiol.

Thus the present invention provides a method of treating HCV-containing samples with a treating agent containing; (1) an acidifying agent, (2) an amphoteric surfactant or a cationic surfactant having both a straight chain alkyl group of 10 or more carbon atoms and a tertiary amine or a quaternary ammonium salt in a molecule, and (3) a protein-denaturing agent, a nonionic surfactant or a reducing agent to effect the release of the HCV antigen and the destruction of antibodies that bind to the HCV antigen.

It was also found that the effect of the present invention can be enhanced by adding a monosaccharide, a disaccharide, citric acid, or a citrate in addition to or in place of (3) a protein-denaturing agent, a nonionic surfactant or a reducing agent.

As an amphoteric surfactant having both a straight chain alkyl group of 10 or more carbon atoms and a tertiary amine or a quaternary ammonium salt in a molecule, N-dodecyl-N, N-dimethyl-3-ammonio-1-propanesulfonate, N-tetradecyl-N,N-dimethyl-3-ammonio-1-propanesulfonate, N-hexadecyl-N,N-dimethyl-3-ammonio-1-propanesulfonate, N-octadecyl-N,N-dimethyl-3-ammonio-1-propanesulfonate and the like are suitable.

As a cationic surfactant having both a straight chain alkyl group of 10 or more carbon atoms and a tertiary amine or a quaternary ammonium salt in a molecule, decyltrimethylammonium chloride, dodecyltrimethylammonium chloride, tetradecyltrimethylammonium chloride, hexadecyltrimethylammonium chloride, decyltrimethylammonium bromide, dodecyltrimethylammonium bromide, tetradecyltrimethylammonium bromide, hexadecyltrimethylammonium bromide, lauryl pyridinium chloride, tetradecyl pyridinium chloride, cetyl pyridinium chloride, and the like are suitable.

The concentration of such an amphoteric surfactant or a cationic surfactant having both a straight chain alkyl group of 10 or more carbon atoms and a tertiary amine or a quaternary ammonium salt in a molecule is preferably 0.1% or more and 15% or less, and more preferably 0.5-10% at the treatment.

As a nonionic surfactant in the presence of an acidifying agent and an amphoteric surfactant or a cationic surfactant having both a straight chain alkyl group of 10 or more carbon atoms and a tertiary amine or a quaternary ammonium salt in a molecule, polyoxyethylene isooctylphenyl ethers such as Triton X-100, polyoxyethylene nonylphenyl ethers such as NP40, polyoxyethylene sorbitane alkylesters such as Tween 80 or the like is suitable, and their concentration at the treatment is preferably 1% or more and 7.5% or less, and more preferably 1% or more and 5% or less. The percentage as used herein is expressed in weight/weight×100%.

As a protein-denaturing agent in the presence of an acidifying agent and an amphoteric surfactant or a cationic surfactant having both a straight chain alkyl group of 10 or more carbon atoms and a tertiary amine or a quaternary ammonium salt in a molecule, urea and thiourea are suitable, and their concentration at the treatment is preferably 0.5M or more, and more preferably 1M or more and 4M or less, and when the solubility does not count, for example when urea has previously added in the powder form in a sample treatment tube, concentrations up to 10M can be used.

As a reducing agent in the presence of an acidifying agent and an amphoteric surfactant or a cationic surfactant having both a straight chain alkyl group of 10 or more carbon atoms and a tertiary amine or a quaternary ammonium salt in a molecule, cysteine, cysteamine, dimethylaminoethanethiol, diethylaminoethanethiol, diisopropylaminoethanethiol and the like are suitable, and their concentration at the treatment is preferably 0.25 mM or more and 1000 mM or less, and more preferably 1.5 mM or more and 200 mM or less.

As a monosaccharide or a disaccharide to be added to an acidifying agent and an amphoteric surfactant or a cationic surfactant having both a straight chain alkyl group of 10 or more carbon atoms and a tertiary amine or a quaternary ammonium salt in a molecule, maltose, sucrose, trehalose, mannose, fructose, glucose, sorbitol, galactose, and dextrose are suitable. As a citric acid or a citrate to be added to an acidifying agent and an amphoteric surfactant or a cationic surfactant having both a straight chain alkyl group of 10 or more carbon atoms and a tertiary amine or a quaternary ammonium salt in a molecule, citric acid, citric acid hydrate, sodium citrate, and potassium citrate are suitable.

As another substance to be added to the acidifying agent, a protein-denaturing agent such as urea may be contemplated. A protein-denaturing agent such as urea is known to have an effect of partially destroying the higher structure of protein by weakening hydrogen ion bonding, and is capable of destroying the membrane of virus particles or denaturing antibodies against the target antigen. It also has an effect of solubilizing a recombinant protein expressed in, for example, *Escherichia coli* from the inclusion body which is an insoluble fraction. However, in the presence of a protein-denaturing agent such as urea, the structural epitope of the target antigen may also be destroyed, and the biding with a probe such as a antigen-capturing antibody is weakened, posing a serious problem of reduced sensitivity.

On the other hand, the denaturing activity of a protein-denaturing agent may often be reversible, and thus reduction of the concentration of protein denaturing agent by dilution or dialysis may recover the temporary denatured structure. This clearly means that there are test sample-derived antibodies that may compete with a target antigen-capturing probe or a detecting probe, with a result that sensitivity may be reduced. Thus, the addition of a protein-denaturing agent such as urea has such an ambivalent nature.

The present inventors have found that by combining the acid treatment with the treatment by a protein-denaturing agent, the problem associated with the treatment by a protein-denaturing agent such as the reversible denaturing of antibodies in test samples can be resolved, and thereby have completed another embodiment in the present invention.

The present inventors have found that precipitate formation by acid treatment can be greatly reduced by adding urea, one of the protein-denaturing agents, at 1M or more at the treatment. As such a protein-denaturing agent, urea, thiourea etc. are suitable. The concentration of the protein-denaturing agent at the treatment is preferably 1M or more, and more preferably 1.5M or more and 8M or less. Furthermore, it was also found that the addition of a nonionic surfactant such as a polyoxyethylene isooctylphenyl ether such as Triton X-100 and a polyoxyethylene nonylphenyl ether such as NP40 to a treating agent comprising an acidifying agent and a protein-denaturing agent has an effect of enhancing sensitivity. It is also possible to add a reducing agent to a treating agent comprising an acidifying agent and a protein-denaturing agent.

To summarize the above, the present invention provides a method of treating HCV-containing samples which method comprises treating samples containing hepatitis C virus (HCV) with a treating agent comprising (1) an acidifying agent, and (2) a protein-denaturing agent or an amphoteric surfactant or a cationic surfactant having both a straight chain alkyl group of 10 or more carbon atoms and a tertiary amine or a quaternary ammonium salt in a molecule, to effect the release of the HCV antigen and the inactivation of antibodies that bind to the HCV antigen.

The present invention also provides a method of treating HCV-containing samples which method comprises treating the HCV-containing samples with a treating agent comprising at least one substance of the following (1) and (2), and at least one substance of the following (3) to effect the release of the HCV antigen and the inactivation of antibodies that bind to the HCV antigen.

Substances of (1), (2) and (3) are (1) an acidifying agent, (2) a protein-denaturing agent, and (3) a nonionic surfactant or a reducing agent. Furthermore, the treatment of the present invention may be performed at high temperatures, but preferably it is performed at 20° C.-50° C., and more preferably at 25° C.-42° C.

By using the treatment method of the present invention, it is evident that virus antigens can be released from test samples containing virus particles having a structure similar to HCV into a state suitable for a determination method that employs a probe. As used herein, viruses having a structure similar to HCV refer to viruses that form a virus particle having a structure comprising a protein that packs genomic RNA or DNA, a membrane protein and a lipid membrane encircling it, viruses that form a virus particle having a structure comprising a protein that packs genomic RNA or DNA and a membrane protein encircling it, or viruses that form a virus particle having a structure comprising a protein containing genomic RNA or DNA therein and a lipid membrane.

For example, flaviviruses that are related to HCV and retroviruses such as human immunodeficiency virus, and the like are included. Also included are those viruses that have DNA as the genome such as hepatitis B virus having genomic DNA, human Parvoviruses that do not have an envelope protein but have a protein packing genomic DNA, and the like.

EXAMPLES

The present invention will now be explained with reference to the following Examples, but it should understood that these Examples do not limit the scope of the present invention in any way.

Example 1

Method of Preparing a Hybridoma

After a recombinant HCV core protein (Trp C11), prepared by the method described in Japanese Patent No. 3171827, was dissolved in 6M urea, it was diluted in a 10 mM phosphate buffer (pH 7.3) containing 0.15M NaCl to a final concentration of 0.2-1.0 mg/ml, and mixed with an equal amount of Titermax to prepare a Trp C11 emulsion. This emulsion prepared to a final concentration of Trp C11 at 0.1-0.5 mg/ml was intraperitoneally administered to 4-6 week-old BALB/c mice. Two weeks later, they were similarly immunized, and after further 2 weeks a saline in which Trp C11 was prepared at 0.01 mg/ml was administered into the tail vein.

On day 3 after the final immunization, the spleen was aseptically removed from the animals, and was sectioned with scissors, crumbled into individual cells with a mesh, and washed three times in a RPMI 1640 medium. A mouse myeloma cell line SP2/0Ag14 in the logarithmic growth phase from which revertants had been completely removed was cultured for several days in the presence of 8-azaguanidine, and was washed as described above, and then $1.8 \times 10^7$ of this myeloma cells and $1.0 \times 10^8$ of spleen cells were placed in a 50 ml centrifuge tube and were mixed. After centrifuging at 200×g for 5 minutes, the supernatant was removed, to which 1 ml of a RPMI 1640 medium containing 50% polyethylene glycol 4000 (PEG4000; manufactured by Merck) that had been maintained at 37° C. was added for cell fusion.

After PEG4000 was removed by centrifugation (200×g, 5 minutes), the cells were cultured in a RPMI 1640 medium containing hypoxanthine, aminopterin, and thymidine (hereinafter abbreviated as HAT) for 1-2 weeks so that hybridomas may only be grown. Then they were grown in a HAT-free medium, and about two weeks later clones that produce the antibody were examined by ELISA so as to obtain hybridomas that produce the monoclonal antibody of the present invention having the desired specificity.

The hybridomas were subjected to the conventional limiting dilution method for exploring and monocloning the cell lines that produce the antibody, and the each hybridoma was designated as HC11-14, HC11-10, HC11-15, HC11-3, HC11-11, HC11-7, HC11-9, and HC11-21. The hybridomas HC11-14 (FERM BP-6006), HC11-10 (FERM BP-6004), HC11-3 (FERM BP-6002), HC11-11 (FERM BP-6005), and HC11-7 (FERM BP-6003) have been deposited on Jul. 4, 1997, HC11-15 (FERM BP-6782) have been deposited on Jul. 16, 1999, and HC11-9 (FERM BP-08493), and HC11-21 (FERM BP-08494) have been deposited on Sep. 25, 2003 with the Patent Microorganism Depository of the National Institute of Industrial Science and Technology, of Chuo Dai 6, 1-1, Higashi 1-chome, Tsukuba city, Ibaraki Pref., Japan.

Example 2

Preparation of a Monoclonal Antibody

Hybridomas obtained by the method described in Example 1 were intraperitoneally administered to mice that had been treated with pristane etc. and monoclonal antibodies produced in the ascites were harvested. Each monoclonal antibody was purified using a Proten A conjugated Sepharose column.

The isotype of each monoclonal antibody, C11-15, C11-14, C11-10, C11-7, C11-9, C11-11, C11-21 and C11-3, produced from the above 8 hybridomas, respectively, was found to be $IgG_2a$ for C11-10 and C11-7, and $IgG_1$ for C11-14, C11-3, C11-9, C11-21, C11-11 and C11-15 using a mouse Ig isotype kit (manufactured by Zymed). The epitope of each of the monoclonal antibody was determined using peptides comprising about 20 amino acids that were synthesized in a manner that 10 amino acids each from the HCV core region-derived sequences are overlapped. C11-14, C11-10, C11-7 and C11-3 recognized a sequence described in Japanese Patent No. 3171827. C11-9 and C11-21 recognized a sequence $^{21}$DVKFPGGGQIVGGVYLLPR$^{40}$ (SEQ ID NO: 1) and a sequence $^{100}$PRGSRPSWGPTDPRHRSRNVG$^{120}$ (SEQ ID NO: 2), respectively. Thus, C11-9 is a monoclonal antibody that recognizes a sequence of amino acids 21-40 of the HCV core antigen and C11-21 is a monoclonal antibody that recognizes a sequence of amino acids 100-120 of the HCV core antigen.

Example 4

Examination of the Condition for Sample Treatment (Examination of the Treatment Condition)

1) Concentration of an acidifying agent: To 100 µl of the HCV antigen-negative sample and HCV antigen-positive samples (#19, #86, #89, #92-4, #96), 50 µl of each concentration of aqueous hydrochloric acid (HCl) was added, and incubated at 37° C. for 10 minutes. Then 100 µl of them was used as a sample for the assay, and examined in a method described below.

200 µl of anti-HCV core antigen monoclonal antibody (equal amounts of c11-3 and c11-7 were mixed) was added to a 96-well microtiter plate (Costar High Binding Plate) at a concentration of 4 µg/ml, and the plate was incubated overnight at 4° C.

After washing twice with 10 mM phosphate buffer, pH7.3, containing 0.15M NaCl, 350 µl of 10 mM phosphate buffer, pH7.1, containing 0.5% casein sodium was added to each well and the plate was incubated for 2 hours. After removing the blocking solution, 100 µl of the reaction buffer containing a neutralizing agent and each test sample obtained by the sample treatment method were added to each well, and the plate was incubated, with shaking, at room temperature for 1 hour, washed six times with 350 µl of 10 mM phosphate buffer, pH7.3, containing 0.05% Tween 20 (washing solution), and then 200 µl of the peroxidase (HRP)-labelled monoclonal antibody (equal amounts of C11-10 and C11-14 were mixed) was added to each well, and the plate was incubated at room temperature for 30 minutes. It was washed six times with the washing solution, 200 µl of a substrate solution (0.1M citrate phosphate buffer, pH5.0, containing 2 mg/ml of o-phenylene diamine and 0.9 µl/ml of 30% hydrogen peroxide) was added, and then incubated for 30 minutes.

50 µl of 5N sulfuric acid was added to stop the enzymatic reaction, and absorbance was measured using a microplate reader (CORONA MTP32) at 492 nm (a reference wavelength 630 nm) and the result is shown in FIG. 1. The concentration of hydrochloric acid shown in FIG. 1 is expressed in the concentration at the treatment of samples after mixing the sample and the treating agent.

HCV-positive samples (#19, #86, #89, #92-4, #96) that were incubated in a hydrochloric acid-free solution at 37° C. for 10 minutes exhibited virtually no core antigen immuno-reactivity, but at a hydrochloric acid (HCl) concentration of 0.167N or more at the treatment of samples, core antigen immuno-reactivity was noted with peak values being obtained at 0.5-0.867N of HCl. Also in a study in which sulfuric acid was substituted for hydrochloric acid, a similar result was obtained.

2) Concentration of various surfactants in the presence of an acidifying agent: To 100 µl of the HCV antigen-negative sample or HCV antigen-positive samples (#110, #120, #117, #89), 50 µl of various surfactants dissolved in 1.5N aqueous hydrochloric acid was added, and incubated at 37° C. for 10 minutes. 100 µl of the treated-sample was used as a sample for the assay and was subjected to examination in the method described in the above 1) (Table 1 to Table 4).

As shown in Table 1 to Table 4, a surfactant for which 2 of 4 samples exhibited a reactivity higher than the judgment criteria for each sample was judged to have an effect to detect HCV core antigen sensitively. As a result, when each of various surfactants was added together with an acidifying agent such as hydrochloric acid and sulfuric acid, there were some surfactants that greatly enhanced the immunological activity of the HCV antigen in HCV core antigen-positive samples. Surfactants that exhibited the effect of addition were amphoteric surfactants or cationic surfactants having both a straight chain alkyl group of 10 or more carbon atoms and a tertiary amine or a quaternary ammonium salt in a molecule.

Amphoteric surfactants or cationic surfactants having both a straight chain alkyl group of 8 or less carbon atoms and a quaternary ammonium salt in the same molecule had no effect of addition. Nonionic surfactants such as MEGA-10 having both a straight chain alkyl group of 10 carbon atoms and a secondary amine in a molecule had a weak effect of addition. Nonionic surfactants such as Triton X-100 and Tween 20 and surfactants having a steroid backbone such as CHAPS exhibited no enhancement in reactivity. Sodium dodecyl sulfate (SDS) had virtually no effect and caused white precipitation during reaction with samples at concentrations of 2.5% or higher. N-lauroyl sarcosine Na, deoxycholic acid etc. were also examined, but in the presence of an acidifying agent they had poor solubility and could not be subjected to study.

By adding to an acidifying agent an amphoteric surfactant or a cationic surfactant having both a straight chain alkyl group of 10 or more carbon atoms and a tertiary amine or a quaternary ammonium salt in a molecule, enhancement in the sensitivity of measurement was noted. The acidifying agent was removed from the treating agent comprising this acidifying agent and a surfactant, and the surfactant alone that was effective was used in the treatment, but the sensitivity of measurement markedly decreased. This suggested that enhancement in the sensitivity of measurement is based on the acidifying agent, and the addition of a surfactant to the acidifying agent causes the marked enhancement thereof.

TABLE 1

| Surfactant added to 0.5N HCl | Concentration % | HCV core antigen-positive sample | | | |
|---|---|---|---|---|---|
| | | #110 | #120 | #117 | #89 |
| No addition | 0.00 | 0.031 | 0.128 | 0.123 | 0.322 |
| Judging criteria of effect of surfactant addition | | 0.053 | 0.217 | 0.209 | 0.547 |
| Lauryl pyridinium Chloride $[C_3H_5NCH_2(CH_2)_{10}CH_3]Cl$ | 0.50 | 0.069 | 0.305 | 0.598 | 0.542 |
| | 1.25 | 0.086 | 0.362 | 1.120 | 0.611 |
| | 1.67 | 0.128 | 0.304 | 1.038 | 0.559 |
| | 2.50 | 0.025 | 0.232 | 0.823 | 0.660 |
| | 3.33 | 0.064 | 0.062 | 0.757 | 0.415 |
| | 5.00 | 0.010 | 0.015 | 0.123 | 0.227 |
| Cetyl pyridinium Chloride | 0.50 | 0.057 | 0.159 | 0.222 | 0.342 |
| | 1.25 | 0.274 | 0.135 | 0.445 | 0.503 |
| | 2.50 | 0.106 | 0.405 | 0.768 | 0.586 |
| Decyltrimethylammonium Chloride $[CH_3(CH_2)_9N(CH_3)_3]Cl$ | 0.50 | 0.074 | 0.303 | 0.449 | 0.686 |
| | 1.25 | 0.139 | 0.355 | 1.241 | 0.904 |
| | 1.67 | 0.112 | 0.347 | 1.291 | 0.661 |
| | 2.50 | 0.180 | 0.375 | 0.660 | 0.464 |
| | 3.33 | 0.122 | 0.317 | 1.185 | 0.504 |
| | 5.00 | 0.101 | 0.228 | 0.953 | 0.462 |
| Dodecyltrimethylammonium Chloride $[CH_3(CH_2)_{11}N(CH_3)_3]Cl$ | 0.50 | 0.117 | 0.280 | 0.810 | 0.705 |
| | 1.25 | 0.159 | 0.306 | 1.416 | 0.771 |
| | 1.67 | 0.159 | 0.332 | 1.265 | 0.846 |
| | 2.50 | 0.199 | 0.445 | 0.672 | 0.921 |
| | 3.33 | 0.106 | 0.300 | 1.151 | 0.468 |
| | 5.00 | 0.054 | 0.206 | 0.746 | 0.253 |
| Tetradecyltrimethylammonium Chloride $[CH_3(CH_2)_{13}N(CH_3)_3]Cl$ | 0.50 | 0.048 | 0.219 | 0.389 | 0.450 |
| | 1.25 | 0.130 | 0.282 | 0.965 | 0.636 |
| | 1.67 | 0.104 | 0.274 | 0.729 | 0.409 |
| | 2.50 | 0.102 | 0.326 | 0.818 | 0.552 |
| | 3.33 | 0.057 | 0.154 | 0.436 | 0.284 |
| | 5.00 | 0.035 | 0.108 | 0.472 | 0.225 |

TABLE 2

| Surfactant added to 0.5N HCl | Concentration % | HCV core antigen-positive sample | | | |
|---|---|---|---|---|---|
| | | #110 | #120 | #117 | #89 |
| No addition | 0.00 | 0.031 | 0.128 | 0.123 | 0.322 |
| Judging criteria of effect of surfactant addition | | 0.053 | 0.217 | 0.209 | 0.547 |
| Hexdecyltrimethylammonium Chloride $[CH_3(CH_2)_{15}N(CH_3)_3]Cl$ | 0.50 | 0.021 | 0.204 | 0.147 | 0.388 |
| | 1.25 | 0.188 | 0.180 | 0.624 | 0.537 |
| | 1.67 | 0.138 | 0.088 | 0.446 | 0.373 |
| | 3.33 | 0.066 | 0.144 | 0.316 | 0.182 |
| | 5.00 | 0.034 | 0.100 | 0.211 | 0.236 |
| Hexyltrimethylammonium Bromide $[CH_3(CH_2)_5N(CH_3)_3]Br$ | 1.67 | 0.019 | 0.056 | 0.092 | 0.180 |
| | 3.33 | 0.018 | 0.032 | 0.087 | 0.122 |
| | 5.00 | 0.015 | 0.028 | 0.082 | 0.085 |
| Octyltrimethylammonium Bromide $[CH_3(CH_2)_7N(CH_3)_3]Br$ | 1.67 | 0.047 | 0.115 | 0.402 | 0.349 |
| | 3.33 | 0.039 | 0.078 | 0.429 | 0.317 |
| | 5.00 | 0.007 | 0.063 | 0.322 | 0.198 |
| Decyltrimethylammonium Bromide $[CH_3(CH_2)_9N(CH_3)_3]Br$ | 1.67 | 0.122 | 0.427 | 1.253 | 0.779 |
| | 3.33 | 0.143 | 0.441 | 1.308 | 0.730 |
| | 5.00 | 0.153 | 0.341 | 1.126 | 0.657 |
| Dodecyltrimethylammonium Bromide $[CH_3(CH_2)_{11}N(CH_3)_3]Br$ | 0.50 | 0.100 | 0.274 | 0.955 | 0.628 |
| | 1.67 | 0.147 | 0.259 | 1.206 | 0.597 |
| | 3.33 | 0.141 | 0.317 | 1.326 | 0.639 |
| | 5.00 | 0.133 | 0.341 | 1.374 | 0.560 |
| Tetradecyltrimethylammonium Bromide $[CH_3(CH_2)_{13}N(CH_3)_3]Br$ | 1.67 | 0.105 | 0.146 | 0.499 | 0.567 |
| | 3.33 | 0.076 | 0.325 | 0.793 | 0.522 |
| | 5.00 | 0.057 | 0.215 | 0.532 | 0.306 |
| Hexadecyltrimethylammonium Bromide $[CH_3(CH_2)_{15}N(CH_3)_3]Br$ | 1.67 | 0.178 | 0.063 | 0.293 | 0.285 |
| | 3.33 | 0.311 | 0.349 | 0.799 | 0.600 |
| | 5.00 | −0.109 | 0.298 | 0.610 | 0.369 |

TABLE 3

| Surfactant added to 0.5N HCl | Concentration % | HCV core antigen-positive sample | | | |
|---|---|---|---|---|---|
| | | #110 | #120 | #117 | #89 |
| No addition | 0.00 | 0.031 | 0.128 | 0.123 | 0.322 |
| Judging criteria of effect of surfactant addition | | 0.053 | 0.217 | 0.209 | 0.547 |
| 3-[(3-Cholamidopropyl)dimethyl-ammonio]-1-propanesulfonate | 1.67 | 0.022 | 0.014 | 0.049 | 0.081 |
| | 3.33 | 0.026 | −0.009 | 0.016 | 0.060 |
| | 5.00 | 0.027 | 0.000 | 0.033 | 0.082 |
| N-Dodecyl-N,N-dimethyl-3-ammonio-1-propanesulfonate $CH_3(CH_2)_{11}N(CH_3)_2[(CH_2)_3SO_3]$ | 1.67 | 0.107 | 0.288 | 1.044 | 0.748 |
| | 2.00 | 0.059 | 0.278 | 0.853 | 0.705 |
| | 3.33 | 0.122 | 0.372 | 1.353 | 0.802 |
| | 5.00 | 0.115 | 0.360 | 1.335 | 0.860 |
| | 10.00 | 0.071 | 0.234 | 1.048 | 0.746 |
| N-Tetradecyl-N,N-dimethyl-3-ammonio-1-propanesulfonate $CH_3(CH_2)_{13}N(CH_3)_2[(CH_2)_3SO_3]$ | 1.67 | 0.103 | 0.301 | 0.626 | 0.808 |
| | 3.33 | 0.146 | 0.376 | 1.149 | 0.890 |
| | 5.00 | 0.171 | 0.467 | 1.277 | 0.893 |
| N-Hexadecyl-N,N-dimethyl-3-ammonio-1-propanesulfonate $CH_3(CH_2)_{15}N(CH_3)_2[(CH_2)_3SO_3]$ | 1.67 | 0.135 | 0.198 | 0.301 | 0.577 |
| | 3.33 | 0.150 | 0.488 | 0.643 | 1.104 |
| | 5.00 | 0.147 | 0.459 | 0.877 | 1.471 |
| N-Octadecyl-N,N-dimethyl-3-ammonio-1-propanesulfonate $CH_3(CH_2)_{17}N(CH_3)_2[(CH_2)_3SO_3]$ | 1.67 | 0.086 | 0.147 | 0.195 | 0.483 |
| | 3.33 | 0.096 | 0.206 | 0.211 | 0.863 |
| | 5.00 | 0.067 | 0.189 | 0.259 | 1.448 |
| MEGA10 n-Decanoyl-N-methylglucamide | 1.67 | 0.048 | 0.058 | 0.163 | 0.333 |
| | 3.33 | 0.046 | 0.022 | 0.160 | 0.330 |
| | 5.00 | 0.033 | 0.006 | 0.148 | 0.422 |

TABLE 4

| Surfactant added to 0.5N HCl | Concentration % | HCV core antigen-positive sample | | | |
|---|---|---|---|---|---|
| | | #110 | #120 | #117 | #89 |
| No addition | 0.00 | 0.031 | 0.128 | 0.123 | 0.322 |
| Judging criteria of effect of surfactant addition | | 0.053 | 0.217 | 0.209 | 0.547 |
| TritonX-100 | 1.67 | 0.016 | 0.069 | 0.086 | 0.365 |
| | 3.33 | 0.026 | 0.047 | 0.149 | 0.380 |
| | 5.00 | 0.060 | 0.053 | 0.166 | 0.388 |
| TritonX-114 | 1.67 | 0.030 | 0.097 | 0.164 | 0.364 |
| | 3.33 | 0.022 | 0.065 | 0.166 | 0.351 |
| | 5.00 | 0.169 | 0.023 | 0.139 | 0.169 |
| Tween20 | 1.67 | 0.033 | 0.097 | 0.137 | 0.352 |
| | 3.33 | 0.035 | 0.087 | 0.142 | 0.368 |
| | 5.00 | 0.038 | 0.069 | 0.164 | 0.353 |
| Tween80 | 1.67 | 0.033 | 0.118 | 0.176 | 0.436 |
| | 3.33 | 0.026 | 0.096 | 0.174 | 0.425 |
| | 5.00 | 0.017 | 0.078 | 0.148 | 0.461 |
| Sodium dodecyl sulfate | 0.50 | 0.023 | 0.085 | 0.210 | 0.476 |
| | 1.25 | −0.044 | −0.085 | 0.130 | 0.237 |
| Dodecyltrimethylammonium Bromide | 1.67 | 0.146 | 0.150 | 0.808 | 0.469 |
| 0.5N $H_2SO_4$ was used instead of 0.5N HCl | 3.33 | 0.102 | 0.174 | 0.835 | 0.418 |
| | 5.00 | 0.030 | 0.134 | 0.633 | 0.290 |

3) A protein-denaturing agent in the presence of an acidifying agent

To 100 μl of the HCV antigen-negative sample or HCV antigen-positive samples (#86, #96, #117, #89), 50 μl of urea, a protein-denaturing agent, dissolved in 1.5N aqueous hydrochloric acid was added, and incubated at 37° C. for 10 minutes. 100 μl of the treated-sample was used as a sample for the assay and was subjected to examination in the method described in the above 1) (Table 5).

By adding urea, a protein-denaturing agent, some samples exhibited an enhancement by 1.4-2-fold as compared to the control in which an acidifying agent was only added. In the treatment with an acidifying agent alone, it may denature serum proteins and may cause precipitation or cloudiness, which may often cause clogging in pipetting of sample and provide a major cause for false positives. Furthermore, the target antigen may be entangled into those precipitates, which is likely to reduce sensitivity. The addition of urea at 1M or more at the treatment of samples, it was found, can markedly reduce the formation of such precipitates, and in particular the addition of 1.5M or more and 1M or less at the treatment of samples proved to be effective. Though urea can be dissolved to about a 10M solution, precipitation may occur depending on the storage condition, and thus when it was used as a solution, the concentration at the treatment of samples depends on the ratio of the sample-treatment solution volume and the test sample volume.

TABLE 5

| | Control | | |
|---|---|---|---|
| HCl (N) | 0.5 | 0.5 | |
| Urea (M) | — | 2.67 | |
| | Absorbance | Absorbance | % relative to control |
| Normal serum | 0.012 | 0.011 | 91.3 |
| HCV antigen-positive sample | | | |
| #117 | 0.111 | 0.267 | 240.5 |
| #89 | 0.256 | 0.357 | 139.5 |
| #96 | 0.403 | 0.594 | 147.4 |
| #86 | 0.575 | 0.614 | 106.8 |

4) Examination of a nonionic surfactant in the presence of an acidifying agent, and an amphoteric surfactant or a cationic surfactant having both a straight chain alkyl group of 10 or more carbon atoms and a tertiary amine or a quaternary ammonium salt in a molecule:

To 100 µl of the HCV antigen-negative sample (normal plasma) or three HCV antigen-positive samples (#120, #117, #97), 100 µl of a solution in which Triton X-100, a nonionic surfactant, was mixed with a solution comprising 1.0N hydrochloric acid and 5.0% dodecyltrimetylammonium bromide (abbreviated as C12TAB) was added, and incubated at 37° C. for 10 minutes. 100 µl of the treated-sample was used as a sample for the assay and was subjected to examination in the method described in the above 1) (FIG. 2).

The concentration of Triton X-100, a nonionic surfactant, shown in FIG. 2 was expressed in the concentration at the treatment of samples. The addition of Triton X-100 to the HCV antigen-negative sample (normal plasma) caused virtually no changes in signals, but for HCV antigen-positive samples (#120, #117, #97), the immuno-reactivity increased by the addition of Triton X-100 at concentrations of 1%-7.5% at the treatment of samples. The particularly high immuno-reactivity was observed at the concentration of 1%-5% of Triton X-100.

5) Examination of a protein-denaturing agent in the presence of an acidifying agent, and an amphoteric surfactant or a cationic surfactant having both a straight chain alkyl group of 10 or more carbon atoms and a tertiary amine or a quaternary ammonium salt in a molecule:

100 µl of a solution in which urea, a protein-denaturing agent, was mixed with a solution comprising 1.0N hydrochloric acid and 5.0% C12TAB was added to 100 µl of the HCV antigen-negative sample (normal plasma) or four HCV antigen-positive samples (#120, #118, #117, #97), and incubated at 37° C. for 10 minutes. 100 µl of the treated-sample was used as a sample for the assay and was subjected to examination in the method described in the above 1). The ratio of immunological activity of each HCV antigen-positive sample to the HCV antigen-negative sample (absorbance of a HCV antigen-positive sample/absorbance of the HCV antigen-negative sample) is shown in Table 6.

TABLE 6

| | | HCV antigen-positive sample | | | |
|---|---|---|---|---|---|
| Urea(M) | Normal plasma | #97 | #117 | #118 | #120 |
| 0.0 | 1.0 | 22.3 | 23.1 | 3.4 | 9.7 |
| 0.5 | 1.0 | 31.7 | 35.1 | 4.5 | 13.7 |
| 1.0 | 1.0 | 28.0 | 45.0 | 4.3 | 11.4 |
| 1.5 | 1.0 | 52.8 | 77.3 | 8.3 | 21.9 |
| 2.0 | 1.0 | 65.2 | 82.4 | 7.8 | 25.4 |
| 2.5 | 1.0 | 94.6 | 96.2 | 9.7 | 30.4 |
| 3.0 | 1.0 | 155.8 | 142.0 | 13.8 | 36.7 |
| 3.5 | 1.0 | 232.3 | 216.3 | 16.0 | 49.3 |

The concentration of urea, a protein-denaturing agent, shown in Table 6 was expressed in the concentration at the treatment of samples. The ratio of immunological activity of a HCV antigen-positive sample (#120, #117, #97) to the HCV antigen-negative sample markedly increased by the addition of urea at 0.5M or more, and continued to increase with increased concentration of urea to at least 3.5M. In the present study, the solubility of the sample-treatment solution containing 8M Urea was poor, and thus urea at 4M or more at the treatment of samples could not be examined.

Thus, it was confirmed that the simultaneous presence of a reagent for use as a protein-denaturing agent leads to increased immunological activity of the HCV core antigen. On the effect of coexistence of these substances, similar results are expected to be confirmed for protein-denaturing agents except for urea.

6) Examination of a reducing agent in the presence of an acidifying agent, and an amphoteric surfactant or a cationic surfactant having both a straight chain alkyl group of 10 or more carbon atoms and a tertiary amine or a quaternary ammonium salt in the same molecule:

100 µl of a solution in which diethylaminoethanethiol hydrochloride, a reducing agent, was mixed with a solution comprising 1.0N hydrochloric acid and 5.0% C12TAB was added to 100 µl of the HCV antigen-negative sample (normal plasma) or three HCV antigen-positive samples (#120, #117, #97), and incubated at 37° C. for 10 minutes. 100 µl of the treated-sample was used as a sample for the assay and was subjected to examination in the method described in the above 1) (Table 7).

The concentration of diethylaminoethanethiol hydrochloride, a reducing agent, was expressed in the concentration at the treatment of samples. In the HCV antigen-negative sample (normal plasma), the addition of diethylaminoethanethiol hydrochloride caused virtually no changes in signals, but for HCV antigen-positive samples (#120, #117, #97), the addition of the reducing agent at concentrations of 0.25 mM or more led to enhancement in signals, at reducing agent concentrations of 10 mM or more, in particular, the enhancement of 30% or more was observed in all three samples, and in #117 the addition of a 20 mM reducing agent enhanced signals by 2-fold or more.

TABLE 7

| | | HCV antigen-positive sample | | | | | |
|---|---|---|---|---|---|---|---|
| Diethylaminoethanethiol | Normal | #120 | | #117 | | #97 | |
| hydrochloride (mM) | plasma OD | OD | % of control | OD | % of control | OD | % of control |
| 0(Control) | 0.034 | 0.382 | 100% | 0.927 | 100% | 0.473 | 100% |
| 0.25 | 0.045 | 0.436 | 114% | 1.258 | 136% | 0.538 | 114% |

TABLE 7-continued

| Diethylaminoethanethiol hydrochloride (mM) | Normal plasma OD | #120 HCV antigen-positive sample | | #117 | | #97 | |
|---|---|---|---|---|---|---|---|
| | | OD | % of control | OD | % of control | OD | % of control |
| 0.50 | 0.029 | 0.454 | 119% | N.T | N.T | 0.543 | 115% |
| 1.0 | 0.037 | 0.483 | 126% | N.T | N.T | 0.611 | 129% |
| 1.5 | 0.033 | 0.503 | 132% | 1.222 | 132% | 0.692 | 146% |
| 10.0 | 0.024 | 0.507 | 133% | 1.303 | 141% | 0.687 | 145% |
| 15.0 | 0.030 | 0.550 | 144% | 1.831 | 198% | 0.729 | 154% |
| 20.0 | 0.022 | 0.549 | 144% | 1.930 | 208% | 0.752 | 159% |
| 30.0 | 0.023 | 0.509 | 133% | N.T | N.T | 0.774 | 164% |
| 40.0 | 0.024 | 0.557 | 146% | 1.462 | 158% | 0.723 | 153% |
| 50.0 | 0.033 | 0.570 | 149% | 1.650 | 178% | 0.748 | 158% |

N.T: Not tested

Example 5

Detection of the HCV Core Antigen using the Treatment Method of the Present Invention and the Conventional Treatment Method (1)

Japanese Patent No. 3171827 and Aoyagi et al.'s report (Journal of Clinical Microbiology 37: 1802-1808, 1999) indicates that by a 30-minute heat treatment with a treatment solution comprising a high concentration of a anionic surfactant such as sodium dodecyl sulfate and an amphoteric surfactant, the HCV core antigen can be detected at high sensitivity. This sample-treatment method and the method of the present invention were used to detect the HCV core antigen in test samples and were compared.

<Determination of the HCV Core Antigen Using the Treatment Method of the Present Invention>

100 μl of a test sample and 100 μl of a sample-treatment solution (1N HCl, 7% C12TAB, 3.5% N-hexadecyl 1-N,N-dimethyl-3-ammonio-1-propanesulfonate, 7% Triton X-100, 2M urea, 10 mM diethylaminoethanethiol hydrochloride) were mixed, which was incubated at 37° C. for 10 minutes.

To each well of a 96-well microtiter plate (Costar high binding plate), 200 μl of anti-HCV core antigen monoclonal antibody (equal amounts of C11-3 and C11-7 were mixed) at 4 μg/ml was added and the plate was incubated overnight at 4° C. After washing twice with 10 mM phosphate buffer, pH 7.3, containing 0.15M NaCl, 350 μl of 10 mM phosphate buffer, pH 7.1, containing 0.5% casein sodium was added, and the plate was incubated for 2 hours. After removing the blocking solution, 100 μl of the reaction buffer containing a neutralizing agent and 100 μl of a treated sample were added to each well.

The plate was incubated with shaking at room temperature for 1 hour, and was washed six times with 350 μl of 10 mM phosphate buffer, pH 7.3, containing 0.05% Tween 20 (washing solution). 200 μl of a HRP-labelled monoclonal antibody (equal amounts of C11-10 and C11-14 were mixed) was added to each well and incubated at room temperature for 30 minutes. It was washed six times with the washing solution, 200 μl of the substrate solution (0.1M citrate phosphate buffer, pH 5.0, containing 2 mg/ml o-phenylene diamine and 0.9 μl/ml of 30% hydrogen peroxide) was added thereto and incubated for 30 minutes. 50 μl of 5N sulfuric acid was added to stop the reaction, and absorbance was measured using a microplate reader (CORONA MTP32) at 492 nm (a reference wavelength 630 nm).

<Determination of the HCV Core Antigen Using the Conventional Treatment Method>

100 μl of a sample and 50 μl of a treatment solution (15% SDS, 2% CHAPS, 0.3% Triton X-100, 2M urea) were mixed, which was treated at 56° C. for 30 minutes. After returning to room temperature, 100 μl of treated-sample was used as a sample for the assay.

To each well of a 96-well microtiter plate (Costar high binding plate), 200 μl of the anti-HCV core antigen monoclonal antibody (equal amounts of C11-3 and C11-7 were mixed) at 4 μg/ml was added and the plate was incubated overnight at 4° C. After washing twice with 10 mM phosphate buffer, pH 7.3, containing 0.15M NaCl, 350 μl of 10 mM phosphate buffer, pH 7.1, containing 0.5% casein sodium was added, and the plate was incubated for 2 hours. After removing the blocking solution, 100 μl of the reaction buffer and 100 μl of the treated sample were added to each well.

The plate was incubated with shaking at room temperature for 1 hour, and was washed six times with 350 μl of 10 mM phosphate buffer, pH 7.3, containing 0.05% Tween 20 (washing solution). 200 μl of the HRP-labelled monoclonal antibody (equal amounts of C11-10 and C11-14 were mixed) was added to each well and incubated at room temperature for 30 minutes. It was washed six times with the washing solution, 200 μl of the substrate solution (0.1M citrate phosphate buffer, pH 5.0, containing 2 mg/ml o-phenylene diamine and 0.9 μl of 30% hydrogen peroxide) was added thereto and incubated for 30 minutes. 50 μl of 5N sulfuric acid was added to stop the reaction, and absorbance was measured using a microplate reader (CORONA MTP32) at 492 nm (a reference wavelength 630 nm).

The results of detection of the HCV core antigen using the above two methods are shown in Table 8 and Table 9, and their correlation is shown in FIG. 3. As shown in Table 8 and Table 9, the treatment method of the present invention exhibited enhancement in reactivity for 30 cases of HCV-RNA-positive samples by 1.85-6.7-fold with an mean of 3.6-fold enhancement in reactivity compared to the conventional method. In particular, for 5 samples (No. 9, 11, 24, 25, 30) which could not be detected by the conventional method, the HCV core antigen was easily detected by the treatment method of the present invention, exhibiting a higher sensitivity. The coefficient of correlation was 0.894, indicating a high correlation.

TABLE 8

| Normal healthy sample | Treatment method | | |
|---|---|---|---|
| | Conventional treatment method Absorbance | Inventive treatment method Absorbance | Inventive treatment method vs conventional method |
| NS1 | 0.026 | 0.035 | |
| NP1 | 0.012 | 0.025 | |
| S222 | 0.019 | 0.005 | |
| S223 | 0.010 | 0.008 | |
| S225 | 0.011 | 0.008 | |
| S226 | 0.089 | 0.022 | |
| S229 | 0.082 | 0.017 | |
| S236 | 0.085 | 0.010 | |
| S237 | 0.023 | 0.017 | |
| S239 | 0.023 | 0.023 | |
| mean | 0.038 | 0.017 | 0.45 |

TABLE 9

| HCV-RNA-positive sample | Treatment method | | |
|---|---|---|---|
| | Conventional method Absorbance | Inventive treatment method Absorbance | Inventive treatment method vs conventional method |
| 1 | 0.110 | 0.408 | 3.71 |
| 2 | 0.330 | 1.461 | 4.43 |
| 3 | 0.265 | 0.778 | 2.94 |
| 4 | 0.246 | 0.936 | 3.80 |
| 5 | 0.931 | 1.967 | 2.11 |
| 6 | 0.369 | 1.792 | 4.86 |
| 7 | 0.174 | 0.500 | 2.87 |
| 8 | 0.220 | 0.961 | 4.37 |
| 9 | 0.023 | 0.066 | 2.87 |
| 10 | 0.320 | 1.121 | 3.50 |
| 11 | 0.011 | 0.074 | 6.73 |
| 12 | 0.265 | 1.643 | 6.20 |
| 13 | 0.074 | 0.221 | 2.99 |
| 14 | 0.563 | 1.987 | 3.53 |
| 15 | 0.357 | 1.304 | 3.65 |
| 16 | 0.064 | 0.275 | 4.30 |
| 17 | 0.573 | 1.595 | 2.78 |
| 18 | 0.068 | 0.357 | 5.25 |
| 19 | 0.439 | 0.928 | 2.11 |
| 20 | 0.181 | 0.419 | 2.31 |
| 21 | 0.055 | 0.199 | 3.62 |
| 22 | 0.054 | 0.137 | 2.54 |
| 23 | 0.041 | 0.131 | 3.20 |
| 24 | 0.020 | 0.037 | 1.85 |
| 25 | 0.026 | 0.067 | 2.58 |
| 26 | 0.055 | 0.217 | 3.95 |
| 27 | 0.332 | 1.088 | 3.28 |
| 28 | 0.119 | 0.544 | 4.57 |
| 29 | 0.319 | 0.990 | 3.10 |
| 30 | 0.020 | 0.082 | 4.10 |
| mean | | | 3.60 |

Example 6

Reactivity by the Combination of Monoclonal Antibodies

100 µl of a sample and 100 µl of the sample-treatment solution (1N HCl, 7% C12TAB, 7% Triton X-100, 2M urea, 10 mM diethylaminoethanethiol hydrochloride) were mixed, and incubated at 37° C. for 10 minutes.

To each well of a 96-well microtiter plate (Costar high binding plate), 200 µl of the anti-HCV core antigen monoclonal antibody (equal amounts of C11-3, C11-7 and C11-21 were mixed) at 4 µg/ml was added and incubated overnight at 4° C. After washing twice with 10 mM phosphate buffer, pH 7.3, containing 0.15M NaCl, 350 µl of 10 mM phosphate buffer, pH 7.1, containing 0.5% casein sodium was added, and the plate was incubated for 2 hours. After removing the blocking solution, 100 µl of the reaction buffer containing a neutralizing agent and 100 µl of a treated sample were added to each well.

The plate was incubated with shaking at room temperature for 1 hour, and was washed six times with 350 µl of 10 mM phosphate buffer, pH 7.3, containing 0.05% Tween 20 (washing solution). 200 µl of the HRP-labelled monoclonal antibody (equal amounts of C11-9 and C11-14 were mixed) was added to each well and incubated at room temperature for 30 minutes. It was washed six times with the washing solution, 200 µl of the substrate solution (0.1M citrate phosphate buffer, pH 5.0, containing 2 mg/ml o-phenylene diamine and 0.9 µl/ml of 30% hydrogen peroxide) was added thereto and incubated for 30 minutes. 50 µl of 5N sulfuric acid was added to stop the reaction, and absorbance was measured using a microplate reader (CORONA MTP32) at 492 nm (a reference wavelength 630 nm), and the result was compared to that obtained in the detection of the HCV core antigen using the sample-treatment method of the present invention in Example 5 (Table 11 and Table 12).

When C11-21 in addition to C11-3 and C11-7 was used in the solid phase, C11-9 instead of C11-10 and C11-14 were used as the labelled antibody, the immuno-reactivity was enhanced by an average of 1.31-fold, and by 1.65-fold for No. 19 (Table 12). This effect is considered to result from the use of three types of antibodies that recognize amino acids 100-120 and 111-130 at the C terminal region of the HCV core antigen as the solid-phase antibody. Thus, when three antibodies that recognize the amino acid sequence 100-130 of the HCV core antigen are used in the solid phase than when two such antibodies are used, the HCV core antigen can be more easily captured, and enhancement in measured values was noted.

Example 7

Reactivity by the Combination of Monoclonal Antibodies

100 µl of a sample and 100 µl of the treatment solution (1N HCl, 7% C12TAB, 7% Triton X-100, 2M urea, 10 mM diethylaminoethanethiol hydrochloride) were mixed, and incubated at 37° C. for 10 minutes.

To each well of a 96-well microtiter plate (Costar high binding plate), 200 µl of the anti-HCV core antigen monoclonal antibody (equal amounts of C11-3 & C11-7, or C11-3 & C11-7 & C11-11, or C11-3 & C11-7 & C11-21 were mixed) at 4 µg/ml in a total was added and the plate was incubated overnight at 4° C. After washing twice with 10 mM phosphate buffer, pH 7.3, containing 0.15M NaCl, 350 µl of 10 mM phosphate buffer, pH 7.1, containing 0.5% casein sodium was added, and incubated for 2 hours. After removing the blocking solution, 100 µl of the reaction buffer containing a neutralizing agent and 100 µl of a treated sample were added to each well.

The plate was incubated with shaking at room temperature for 1 hour, and was washed six times with 350 µl of 10 mM phosphate buffer, pH 7.3, containing 0.05% Tween 20 (washing solution). 200 µl of the HRP-labelled monoclonal antibody (equal amounts of c11-9 and c11-14 were mixed) was added to each well and incubated at room temperature for 30 minutes. It was washed six times with the washing solution, 200 μl of the substrate solution (0.1M citrate phosphate buffer, pH 5.0, containing 2 mg/ml o-phenylene diamine and 0.9 μl/ml of 30% hydrogen peroxide) was added thereto and incubated for 30 minutes. 50 μl of 5N sulfuric acid was added to stop the reaction, and absorbance was measured using a microplate reader (CORONA MTP32) at 492 nm (a reference wavelength 630 nm), and the effect of antibodies addition used in the solid phase was examined (Table 10).

When C11-11 or C11-21 in addition to C11-3 and C11-7 was used in the solid phase, the immuno-reactivity of HCV-RNA-positive samples was enhanced. This effect is considered to result from the use of three types of antibodies that recognize amino acids 100-120 and 111-130 at the C terminal region of HCV core antigen as the solid-phase antibody. Thus, when three antibodies that recognize amino acid sequence 100-130 of HCV core antigen are used in the solid-phase than when two such antibodies are used, the HCV core antigen can be more easily captured, and enhancement in measured values was noted.

Using the combination (antibody combination 1) in which C11-3 & C11-7 (equal amounts were mixed) were immobilized on a plate as the solid phase and C11-14 & C11-10 were used as the enzyme-labelled antibody, and the combination (antibody combination 2) in which C11-3 & C11-7 & C11-21 (equal amounts were mixed) were immobilized on a plate as the solid phase and C11-14 & C11-9 were used as the enzyme-labelled antibody, many HCV-RNA-positive samples were measured, and the results are shown in Table 11 and Table 12. In the HCV-RNA-positive samples, antibody combination 2 gave a higher immuno-reactivity by an average of 1.31-fold than antibody combination 1, and for No. 19 the reactivity increased to a high of about 1.65-fold.

TABLE 10

| Solid phase | C11-3&C11-7 | C11-3&C11-7&C11-11 | C11-3&C11-7&C11-21 |
|---|---|---|---|
| Labelled antibody | | C11-9&C11-14 | |
| | Absorbance | Absorbance | Absorbance |
| Normal plasma | 0.013 | 0.020 | 0.001 |
| Normal Serum 1 | 0.018 | 0.014 | 0.016 |
| Normal Serum 2 | 0.017 | 0.016 | 0.016 |
| Mean of normal | 0.016 | 0.017 | 0.011 |
| HCV-RNA-positive-sample | Absorbance | Absorbance | Absorbance |
| 119 | 0.970 | 1.824 | 1.837 |
| 121 | 0.850 | 1.740 | 1.688 |
| 111 | 0.112 | 0.156 | 0.167 |
| 113 | 0.018 | 0.033 | 0.026 |
| 122 | 0.063 | 0.168 | 0.090 |

TABLE 11

| | Solid phase Labelled antibody | | |
|---|---|---|---|
| Normal sample | Antibody combination (1) C11-3&C11-7 C11-10&C11-14 Absorbance | Antibody combination (2) C11-3&C11-7&C11-21 C11-9&C11-14 Absorbance | Antibody combination (2)/ Antibody combination (1) |
| NS1 | 0.035 | 0.040 | |
| S223 | 0.008 | 0.008 | |
| S226 | 0.022 | 0.019 | |

TABLE 11-continued

| | Solid phase Labelled antibody | | |
|---|---|---|---|
| Normal sample | Antibody combination (1) C11-3&C11-7 C11-10&C11-14 Absorbance | Antibody combination (2) C11-3&C11-7&C11-21 C11-9&C11-14 Absorbance | Antibody combination (2)/ Antibody combination (1) |
| S239 | 0.023 | 0.027 | |
| mean | 0.022 | 0.024 | 1.07 |

TABLE 12

| | Solid phase Labelled Antibody | | |
|---|---|---|---|
| HCV-RNA-positive-sample | Antibody combination (1) C11-3&C11-7 C11-10&C11-14 Absorbance | Antibody combination (2) C11-3&C11-7&C11-21 C11-9&C11-14 Absorbance | Antibody combination (2)/ Antibody combination (1) |
| 1 | 0.408 | 0.591 | 1.45 |
| 2 | 1.461 | 1.636 | 1.12 |
| 3 | 0.778 | 1.088 | 1.40 |
| 4 | 0.936 | 1.327 | 2.42 |
| 5 | 1.967 | 2.683 | 1.36 |
| 6 | 1.792 | 2.300 | 1.28 |
| 7 | 0.500 | 0.670 | 1.34 |
| 8 | 0.961 | 1.311 | 1.36 |
| 9 | 0.066 | 0.076 | 1.15 |
| 10 | 1.121 | 1.493 | 1.33 |
| 12 | 1.643 | 2.156 | 1.31 |
| 13 | 0.221 | 0.327 | 1.48 |
| 14 | 1.987 | 2.633 | 1.33 |
| 15 | 1.304 | 1.762 | 1.35 |
| 16 | 0.275 | 0.357 | 1.30 |
| 17 | 1.595 | 2.317 | 1.45 |
| 18 | 0.357 | 0.349 | 0.98 |
| 19 | 0.928 | 1.531 | 1.65 |
| 20 | 0.419 | 0.587 | 1.40 |
| 21 | 0.199 | 0.179 | 0.90 |
| 22 | 0.137 | 0.205 | 1.50 |
| 24 | 0.037 | 0.036 | 0.97 |
| 25 | 0.067 | 0.090 | 1.34 |
| 26 | 0.217 | 0.250 | 1.15 |
| 27 | 1.088 | 1.473 | 1.35 |
| 29 | 0.990 | 1.342 | 1.36 |
| mean | | | 1.31 |

Example 8

Examination of the Necessity of an Acidifying Agent

100 μl of a sample (normal human serum and three HCV core antigen-positive samples) and 100 μl of the sample-treatment solution excluding an acidifying agent (7% C12TAB, 3.5% N-hexadecyl-N,N-dimethyl-3-ammonio-1-propanesulfonate, 7% Triton X-100, 2M urea, 10 mM diethylaminoethanethiol hydrochloride) were mixed, and incubated at 37° C. for 10 minutes. To each well of a 96-well microtiter plate (Costar high binding plate), 200 μl of the anti-HCV core antigen monoclonal antibody (equal amounts of C11-3 and C11-7 were mixed) at 4 μg/ml was added and the plate was incubated overnight at 4° C. After washing twice with 10 mM phosphate buffer, pH 7.3, containing 0.15M NaCl, 350 μl of 10 mM phosphate buffer, pH 7.1, containing 0.5% casein sodium was added, and the plate was incubated for 2 hours.

After removing the blocking solution, 100 µl of the reaction buffer containing a neutralizing agent and 100 µl of a treated sample were added to each well. The plate was incubated with shaking at room temperature for 1 hour, and was washed six times with 350 µl of 10 mM phosphate buffer, pH 7.3, containing 0.05% Tween 20 (washing solution). 200 µl of the HRP-labelled monoclonal antibody (equal amounts of C11-10 and C11-14 were mixed) was added to each well and incubated at room temperature for 30 minutes. It was washed six times with the washing solution, 200 µl of the substrate solution (0.1M citrate phosphate buffer, pH 5.0, containing 2 mg/ml o-phenylene diamine and 0.9 µl/ml of 30% hydrogen peroxide) was added thereto and incubated for 30 minutes. 50 µl of 5N sulfuric acid was added to stop the reaction, and absorbance was measured using a microplate reader (CO-RONA MTP32) at 492 nm (a reference wavelength 630 nm). The result is shown in Table 13.

TABLE 13

| | Hydrochloric acid concentration (N) at the sample-treatment | | | | | | | |
|---|---|---|---|---|---|---|---|---|
| | 0.00 | 0.13 | 0.25 | 0.38 | 0.50 | 0.63 | 0.75 | 1.00 |
| Normal serum | 0.125 | 0.018 | 0.016 | 0.011 | 0.007 | 0.008 | 0.013 | 0.006 |
| HCV core antigen-positive sample | | | | | | | | |
| #110 | 0.023 | 0.106 | 0.177 | 0.251 | 0.257 | 0.338 | 0.388 | 0.488 |
| #120 | 0.153 | 0.078 | 0.389 | 0.587 | 0.738 | 0.832 | 0.918 | 0.545 |
| #117 | 0.022 | 0.092 | 0.864 | 1.904 | 2.237 | 2.433 | 2.573 | 2.534 |

As shown in Table 13, in each of HCV-positive samples (#110, #120, #117) no core antigen activity was substantially detected when it was incubated in a hydrochloric acid-free solution at 37° C. for 10 minutes, but over a hydrochloric acid concentration of 0.13N at the treatment of samples the core antigen activity started to be noted, and very high core antigen activity was observed at 0.5-1.0N.

Example 9

Method of Preparing a Hybridoma (2)

After a recombinant HCV core protein (I-C173) having a sequence of 1-173 of the HCV genotype 1b-derived core region was dissolved in 6M urea, it was diluted in 10 mM phosphate buffer, pH 7.3, containing 0.15M NaCl to a final concentration of 0.2-1.0 mg/ml, and was mixed with an equal amount of Titermax to prepare a I-C173 emulsion. The emulsion was intraperitoneally administered to 4-6 week-old BALB/c mice. A immunization was carried out every two weeks for three times, and two weeks later a 0.01 mg/ml aqueous solution of I-C173 dissolved in saline was administered into the tail vein. On day 4 after the final immunization, the spleen was aseptically removed from the immunized animals, and was sectioned with scissors, crumbled into individual cells with a mesh, and washed three times in a RPMI 1640 medium. Mouse myeloma cells SP2/0Ag14 in the logarithmic growth phase from which revertants had been completely removed were cultured for several days in the presence of 8-azaguanidine, and were washed as described above, and then $3.26 \times 10^7$ of mouse myeloma cells and $2.28 \times 10^8$ of spleen cells were placed in a 50 ml centrifuge tube and were mixed. After centrifuging at 200×g for 5 minutes, the supernatant was removed, and 1 ml of a RPMI 1640 medium containing 50% polyethylene glycol 4000 (PEG4000; manufactured by Merck) that had been maintained at 37° C. was added for cell fusion. After PEG4000 was removed by centrifugation (200×g, 5 minutes), the cells were cultured in a RPMI 1640 medium containing HAT for 1-2 weeks so that hybridomas only were grown. Then they were grown in a HAT-free medium, and two weeks later clones that produce the antibody were examined so as to obtain hybridomas that produce the monoclonal antibody of the present invention having the desired specificity.

The hybridomas were subjected to the conventional limiting dilution method for exploring and monocloning the cell lines that produce the antibody, and the hybridoma was designated as OT3, which has been deposited on Jun. 1, 2004 with the Patent Microorganism Depositary of the National Institute of Industrial Science and Technology, of Chuo Dai 6, 1-1, Higashi 1-chome, Tsukuba city, Ibaraki Pref., Japan (FERM BP-10032).

Example 10

Preparation of Monoclonal Antibody (2)

Hybridoma obtained by the method described in Example 9 was intraperioneally administered to mice that had been treated with pristane etc. and monoclonal antibody (AOT3) produced in the ascites was harvested. The monoclonal antibody was purified using a Proten A-conjugated Sepharose column. The isotype of AOT3 was found to be $IgG_2b$ using a mouse Ig isotype kit (manufactured by Zymed). The epitope of monoclonal antibody was determined using 20 peptides that were synthesized from HCV core region-derived sequences. AOT3 specifically recognized the sequence $^{101}$RGSRPSWGPTDPRHRSRNVG$^{120}$ (residues 2-21 of SEQ ID NO: 2). AOT3 also exhibited a reactivity to this sequence higher than C11-21.

Example 11

Examination of the Condition for Sample Treatment (2)

(Examination of the Treatment Condition)
1) Maltose concentration: To 100 µl of the HCV antigen-negative sample and HCV antigen-positive samples, 100 µl of a sample-treatment agent (1N HCl, 3.5% C12TAB, 3% N-hexadecyl 1-N,N-dimethyl-3-ammonio-1-propanesulfonate (C16APS), 3% N-octadecyl 1-N,N-dimethyl-3-ammonio-1-propanesulfonate (C18APS), 7% Triton X-100, 3M urea, 20 mM diethylaminoethanethiol hydrochloride) containing each concentration of maltose was added, and the mixture was incubated at 37° C. for 10 minutes. Then 100 µl of the treated-sample was used as a sample for the assay, and examined in a method described below.

To a 96-well microtiter plate (Costar High Binding Plate), 200 µl of the anti-HCV core antigen monoclonal antibody (C11-3, C11-7 and AOT3 were mixed at a ratio of 1:2:1) was added at a concentration of 4 µg/ml, and the plate was incubated overnight at 4° C. After washing twice with 10 mM phosphate buffer, pH7.3, containing 0.15M NaCl, 350 µl of 10 mM phosphate buffer, pH7.1, containing 0.5% casein sodium was added and the plate was incubated for 2 hours. After removing the blocking solution, 100 µl of the reaction buffer containing a neutralizing agent and each treated sample obtained by the sample treatment method were added to each well, and the plate was incubated with shaking at room temperature for 1 hour, washed six times with 350 μl of 10 mM phosphate buffer, pH7.3, containing 0.05% Tween 20 (washing solution), and then 200 μl of the peroxidase (HRP)-labelled monoclonal antibody (equal amounts of C11-9 and C11-14 were mixed) was added thereto, and incubated at room temperature for 30 minutes. It was washed six times with the washing solution, 200 μl of the substrate solution (0.1M citrate phosphate buffer, pH5.0, containing 2 mg/ml of o-phenylene diamine and 0.9 μl/ml of 30% hydrogen peroxide, pH 5.0) was added, and then incubated for 30 minutes. 50 μl of 5N sulfuric acid was added to stop the enzyme reaction, and absorbance was measured using a microplate reader (CORONA MTP32) at 492 nm (a reference wavelength 630 nm) and the result is shown in Table 14. The concentration of maltose shown in Table 14 is expressed in the concentration at the treatment after mixing the sample and the treatment agent.

The HCV core antigen activity in HCV-positive sample was higher in the presence of the maltose concentration of 2.5% than in the absence of maltose, and the activity was also observed at 10% or more. Such an effect was also confirmed for sucrose, fructose, mannose, trehalose, etc. in addition to maltose.

2) Citric acid concentration: To 100 μl of the HCV antigen-negative sample and HCV antigen-positive samples, 100 μl of the treatment agent (1N HCl, 3.5% C12TAB, 3% C16APS, 3% C18APS, 7% Triton X-100, 3M urea, 5% maltose, 20 mM diethylaminoethanethiol hydrochloride) containing each concentration of citric acid was added, and the mixture was incubated at 37° C. for 10 minutes. Then 100 μl of the treated-sample was used as a sample for the assay, and examined in the described above 1) (Table 15). As the addition of citric acid to the treatment agent may cause a slight change in pH of the treated samples, the concentration of the neutralizing agent in 100 μl of the reaction buffer was modified, as appropriate, to be neutral. The concentration of citric acid shown in Table 15 was expressed in the concentration at the treatment after mixing the sample and the treatment agent.

As shown in Table 15, the HCV core antigen activity in each HCV-positive sample was higher in the presence of citric acid concentration of 0.05M than in the absence of citric acid, and the activity was also observed at 0.2M or more. Such an effect was also confirmed for various citrates including sodium citrate.

TABLE 14

| | | HCV antigen-positive sample | | | |
| | Normal | #123 | | #114 | |
| Maltose (%) | serum OD | OD | % of control | OD | % of control |
| --- | --- | --- | --- | --- | --- |
| 0(control) | 0.007 | 0.059 | 100% | 0.057 | 100% |
| 2.5 | 0.016 | 0.081 | 137% | 0.096 | 168% |

TABLE 14-continued

| | | HCV antigen-positive sample | | | |
| | Normal | #123 | | #114 | |
| Maltose (%) | serum OD | OD | % of control | OD | % of control |
| --- | --- | --- | --- | --- | --- |
| 5.0 | 0.012 | 0.122 | 207% | 0.159 | 279% |
| 7.5 | 0.022 | 0.162 | 275% | 0.251 | 440% |
| 10.0 | 0.025 | 0.336 | 569% | 0.503 | 882% |

TABLE 15

| | | HCV antigen-positive sample | | | |
| | Normal | #123 | | #114 | |
| Citric acid (M) | serum OD | OD | % of control | OD | % of control |
| --- | --- | --- | --- | --- | --- |
| 0(control) | 0.016 | 0.122 | 100% | 0.159 | 100% |
| 0.05 | 0.013 | 0.582 | 477% | 0.927 | 583% |
| 0.10 | 0.035 | 0.854 | 700% | 1.032 | 649% |
| 0.15 | 0.028 | 0.676 | 554% | 0.852 | 536% |
| 0.20 | 0.024 | 0.200 | 164% | 0.341 | 214% |

INDUSTRIAL APPLICABILITY

In accordance with the present invention, it is possible to release virus antigen, in a short period of time, from virus particles such as HCV into a state suitable for the immunoassay that detects the antigen using antibody etc. as the probe. In accordance with the present invention, it is also possible to detect and quantify virus antigens more simply, in a short period of time, and at a high sensitivity by the immunoassay that detects the antigen using a probe such as antibody. Also the present invention makes it possible to release virus antigens simply and in a short period of time.

As the useful monoclonal antibody obtained in the present invention specifically recognizes the HCV antigen in a sample of a patient with hepatitis C, it is possible to make a kit for judging the presence of HCV in a sample, a kit for quantifying HCV antigen, and a diagnostic reagent by using each sample treatment method and an immunoassay for hepatitis C. Furthermore, by using the monoclonal antibody obtained according to the present invention and a method of detecting and quantifying hepatitis C virus that employs an extremely simple sample-treatment method, the definite diagnosis of hepatitis C can be made very simply and easily.

The invention claimed is:

1. A method of treating a sample suspected of containing HCV to release HCV antigen and to inactivate antibodies that bind to the HCV antigen, which method comprises treating the sample with a treating agent containing:
   (1) an acidifying agent,
   (2) an amphoteric surfactant or a cationic surfactant having both a straight chain alkyl group of 10 or more carbon atoms and a tertiary amine or a quaternary ammonium salt in the same molecule, and
   either of the following (3), (4) and (5):
   (3) a protein-denaturing agent, a nonionic surfactant or a reducing agent,
   (4) a monosaccharide or a disaccharide, and
   (5) citric acid or a citric acid salt,
   wherein the method effects the release of the HCV antigen and the inactivation of antibodies against the HCV antigen.

2. A method of immunologically detecting HCV core antigen in a sample suspected of containing HCV core antigen, comprising the steps of:
   (1) treating the sample with a treating agent containing:
      (a) an acidifying agent such that the pH in the treated sample is 2.0 or less, and
      (b) a cationic surfactant at a concentration of 0.5 to 10%, wherein the cationic surfactant has both a straight chain alkyl group of 10 or more carbon atoms and a tertiary amine or a quaternary ammonium salt in the same molecule,
   wherein the treatment effects the release of the HCV core antigen and the inactivation of antibodies that bind to the HCV core antigen; then
   (2) reacting the sample treated in the step (1) with a probe that binds to the HCV core antigen; and
   (3) determining if the HCV core antigen binds to the probe.

3. A method according to claim 2 in which said acidifying agent is hydrochloric acid, sulfuric acid, trichloroacetic acid, or trifluoroacetic acid.

4. A method according to claim 2 in which said cationic surfactant having both a straight chain alkyl group of 10 or more carbon atoms and a tertiary amine or a quaternary ammonium salt in the same molecule is decyltrimethylammonium chloride, dodecyltrimethylammonium chloride, tetradecyltrimethylammonium chloride, hexadecyltrimethylammonium chloride, decyltrimethylammonium bromide, dodecyltrimethylammonium bromide, tetradecyltrimethylammonium bromide, hexadecyltrimethylammonium bromide, lauryl pyridinium chloride, tetradecyl pyridinium chloride, or cetyl pyridinium chloride.

5. A method according to claim 1 in which said protein-denaturing agent is urea or thiourea.

6. A method according to claim 1 in which said nonionic surfactant is a polyoxyethylene isooctylphenyl ether, a polyoxyethylene nonylphenyl ether and a polyoxyethylene sorbitan alkylester.

7. A method according to claim 1 in which said reducing agent is cysteine, cysteamine, dimethylaminoethanethiol, diethylaminoethanethiol or diisopropylaminoethanethiol.

8. A method according to claim 1 in which said monosaccharide or disaccharide is maltose, sucrose, trehalose, mannose, fructose, glucose, sorbitol, galactose, or dextrose.

9. A method according to claim 1 in which said citric acid or citric acid salt is citric acid, citric acid hydrate, sodium citrate, or potassium citrate.

10. The method of claim 2, wherein the sample is blood, serum or plasma.

11. The method of claim 2, further comprising neutralizing the pH of the treated sample prior to reacting the sample with the probe.

* * * * *

SEQUENCE LISTING

<160> NUMBER OF SEQ ID NOS: 2

<210> SEQ ID NO 1
<211> LENGTH: 20
<212> TYPE: PRT
<213> ORGANISM: Hepatitis C virus

```
<400> SEQUENCE: 1

Asp Val Lys Phe Pro Gly Gly Gly Gln Ile Val Gly Gly Val Tyr Leu
 1               5                  10                  15

Leu Pro Arg Arg
            20

<210> SEQ ID NO 2
<211> LENGTH: 21
<212> TYPE: PRT
<213> ORGANISM: Hepatitis C virus

<400> SEQUENCE: 2

Pro Arg Gly Ser Arg Pro Ser Trp Gly Pro Thr Asp Pro Arg His Arg
 1               5                  10                  15

Ser Arg Asn Val Gly
            20
```